(12) United States Patent
Tlusty Shapiro et al.

(10) Patent No.: US 11,580,337 B2
(45) Date of Patent: Feb. 14, 2023

(54) MEDICAL OBJECT DETECTION AND IDENTIFICATION

(71) Applicant: International Business Machines Corporation, Armonk, NY (US)

(72) Inventors: Tal Tlusty Shapiro, Zichon Yaacov (IL); Ami Abutbul, Kiryat Gat (IL); Simona Rabinovici-Cohen, Haifa (IL); Shaked Perek, Givatayim (IL); Efrat Hexter, Beit Shemesh (IL)

(73) Assignee: International Business Machines Corporation, Armonk, NY (US)

( * ) Notice: Subject to any disclaimer, the term of this patent is extended or adjusted under 35 U.S.C. 154(b) by 324 days.

(21) Appl. No.: 17/099,199

(22) Filed: Nov. 16, 2020

(65) Prior Publication Data

US 2022/0156506 A1    May 19, 2022

(51) Int. Cl.
| | |
|---|---|
| *G06K 9/00* | (2022.01) |
| *G06K 9/62* | (2022.01) |
| *G16H 30/20* | (2018.01) |
| *G16H 30/40* | (2018.01) |
| *G16H 50/70* | (2018.01) |

(Continued)

(52) U.S. Cl.
CPC ............ *G06K 9/628* (2013.01); *G06K 9/623* (2013.01); *G06V 10/34* (2022.01); *G16H 30/20* (2018.01); *G16H 30/40* (2018.01); *G16H 50/20* (2018.01); *G16H 50/70* (2018.01); *A61B 5/055* (2013.01); *A61B 6/025* (2013.01); *A61B 6/032* (2013.01);

(Continued)

(58) Field of Classification Search
None
See application file for complete search history.

(56) References Cited

U.S. PATENT DOCUMENTS

| | | | | |
|---|---|---|---|---|
| 6,941,016 B1* | 9/2005 | Wagman | .............. | G06V 10/457 382/199 |
| 2007/0092142 A1* | 4/2007 | Kuriathungal | ........ | G06T 7/0012 382/209 |

(Continued)

FOREIGN PATENT DOCUMENTS

| | | |
|---|---|---|
| CN | 106447682 A | 2/2017 |
| CN | 108122605 A | 6/2018 |

(Continued)

OTHER PUBLICATIONS

International Search Report and Written Opinion, International Application No. PCT/IB2021/060345, International Filing Date Nov. 9, 2021.

(Continued)

*Primary Examiner* — Avinash Yentrapati
(74) *Attorney, Agent, or Firm* — Monchai Chuaychoo

(57) ABSTRACT

An approach for improving determining a significant slice associated with a tumor from a volume of medical images is disclosed. The approach is based on the annotation of tumor range and the slice index in which the tumor appears to have the largest area. The approach infer a tumor growth classifier on sliding window of the volume slices and creates a discrete integral function out of the classifier predictions. The approach applies post processing on the discrete integral function which can include a smoothing function and a bias correction. The approach selects the slice index of maximum value from the post processing step.

20 Claims, 5 Drawing Sheets

(51) Int. Cl.
    *G16H 50/20* (2018.01)
    *G06V 10/34* (2022.01)
    *A61B 6/03* (2006.01)
    *G16H 50/50* (2018.01)
    *A61B 5/055* (2006.01)
    *A61B 6/02* (2006.01)

(52) U.S. Cl.
    CPC ......... *G06V 2201/03* (2022.01); *G16H 50/50* (2018.01)

(56) References Cited

U.S. PATENT DOCUMENTS

| | | | |
|---|---|---|---|
| 2011/0026798 A1 | 2/2011 | Madabhushi | |
| 2013/0259345 A1* | 10/2013 | El-Baz | G06T 7/0012 |
| | | | 382/131 |
| 2015/0078640 A1* | 3/2015 | Guo | G06T 7/12 |
| | | | 382/131 |
| 2017/0249739 A1 | 8/2017 | Kallenberg | |
| 2018/0047168 A1* | 2/2018 | Chen | G06T 7/11 |
| 2019/0325249 A1* | 10/2019 | Tahmasebi Maraghoosh | |
| | | | G16H 40/63 |
| 2022/0319008 A1* | 10/2022 | Bengtsson | G06T 7/0016 |

FOREIGN PATENT DOCUMENTS

| | | |
|---|---|---|
| CN | 111091527 A | 5/2020 |
| CN | 109740600 B | 11/2020 |

OTHER PUBLICATIONS

Banerjee, Subhashis, "Brain Tumor Detection and Classification from Multi-Channel MRIs using Deep Learning and Transfer Learning", 2017, 9 pages.

Cui et al., "Malignant lesion segmentation in contrast-enhanced breast MR images based on the marker-controlled watershed", Medical Physics, Oct. 2009, vol. 36, No. 10, pp. 4359-4369.

Doganay et al., "Breast cancer classification from digital breast tomosynthesis using a 3D multi-subvolume approach", SPIE Medical Imaging, 2020, Houston, Texas, United States, 8 pages.

Eltayeb et al., "Automated brain tumor segmentation from multi-slices FLAIR MRI images", Bio-Medical Materials and Engineering I (2019), DOI 10.3233/BME-191066, 15 pages, <https://www.researchgate.net/publication/335514296>.

Fornvik et al., "Breast tomosynthesis: Accuracy of tumor measurement compared with digital mammography and ultrasonography", Acta Radiologica, 2010, DOI 10.3109/02841850903524447, pp. 240-247.

Liu et al., "Fully automatic and segmentation-robust classification of breast tumors based on local texture analysis of ultrasound images", Pattern Recognition 43 (2010), doi: 10.1016/j.patcog.2009.06.002, Accepted Jun. 8, 2009, pp. 280-298.

Nakhmani et al., "MRI Brain Tumor Segmentation and Necrosis Detection Using Adaptive Sobolev Snakes", Proc SPIE Int Soc Opt Eng, Mar. 21, 2014, doi:10.1117/12.2042915, 10 pages.

Pandey et al., "Automatic and fast segmentation of breast region-of-interest (ROI) and density in MRIs", Heliyon, Accepted Dec. 10, 2018, 30 pages, <https://doi.org/10.1016/j heliyon.2018.c01042>.

Tang et al., "Image-based Classification of Tumor Type and Growth Rate using Machine Learning: a preclinical study", Scientific Reports, Published online Aug. 29, 2019, 11 pages, <https://doi.org/10.1038/s41598-019-48738-5>.

* cited by examiner

MEDICAL OBJECT DETECTION AND IDENTIFICATION

BACKGROUND

The present invention relates generally to object detection, and more particularly to detecting medical conditions by leveraging machine learning.

Object detection is a technology related to vision and image processing that defines detecting instances of various objects of a certain environment (e.g., humans, cars, etc.) in digital images and videos. Machine learning (ML) has become a vital part of medical imaging research. Some requires the use of deep learning, a convolutional neural network (e.g., CNN, R-CNN, etc.) for discerning and identified potential problems (e.g., cancer, etc.) based on the medical images.

SUMMARY

Aspects of the present invention disclose a computer-implemented method, a computer system and computer program product for determining a significant slice associated with a tumor from a volume of medical images associated with image analysis. The computer implemented method may be implemented by one or more computer processors and may include classifying medical images from a 3D (3 dimensional) medical image database; defining approximation function on the classified medical images; filtering on the approximation function; and determining a significant slice from the filtered approximation function.

According to another embodiment of the present invention, there is provided a computer system. The computer system comprises a processing unit; and a memory coupled to the processing unit and storing instructions thereon. The instructions, when executed by the processing unit, perform acts of the method according to the embodiment of the present invention.

According to a yet further embodiment of the present invention, there is provided a computer program product being tangibly stored on a non-transient machine-readable medium and comprising machine-executable instructions. The instructions, when executed on a device, cause the device to perform acts of the method according to the embodiment of the present invention.

BRIEF DESCRIPTION OF THE DRAWINGS

Preferred embodiments of the present invention will now be described, by way of example only, with reference to the following drawings, in which.

DETAILED DESCRIPTION

Figure 1:
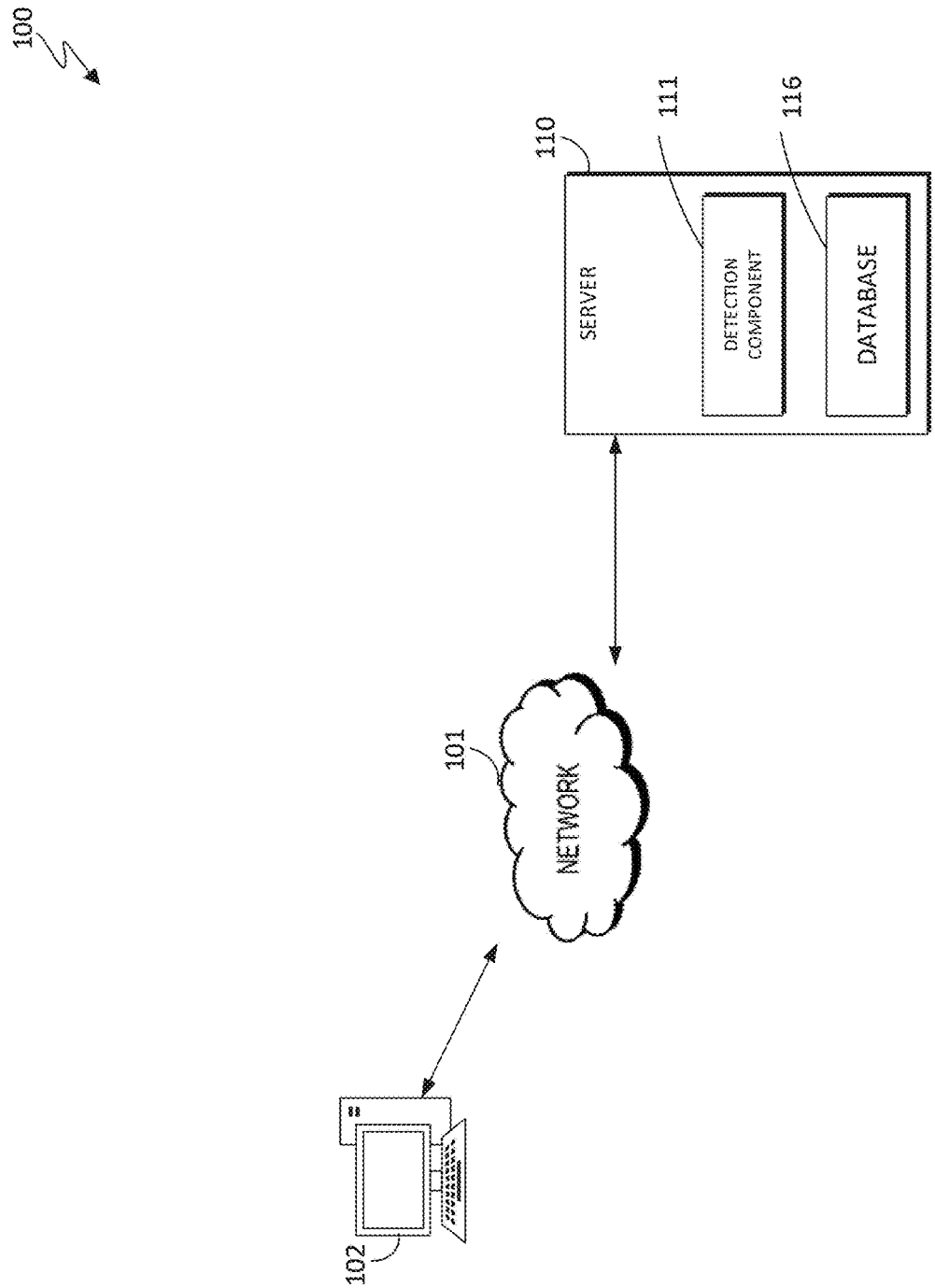
FIG. 1 is a functional block diagram illustrating an image detection model environment, designated as 100, in accordance with an embodiment of the present invention.

In the current state of art of detecting and recognizing tumors from a 3D medical imaging (e.g., MRI, CT, Tomosynthesis, etc.), the existing techniques requires selecting the slice in which the tumor area is the largest among all slices of the volume. This selected slice is often referred as, the significant slice. Likewise, many AI algorithms that analyze tumors in 3D medical imaging, require to have an annotation of the significant slice. Manual annotation of such slice is usually hard work as each volume contains dozens and even hundreds of slices. It requires an annotator/radiologist trained for the specific modality and organ, to find the slices where the tumor is visible, and then select the significant slice among them. This task is tedious, slow, and expensive and requires some mechanism for achieving radiologist's consensus as different radiologists may select different slices as significant.

Embodiments of the present invention recognizes the deficiencies in the current state of art and provides an approach, through the use of machine learning (e.g., CNN, R-CNN, etc.), for automatically selecting the significant slice can ease this task and accelerate the annotation and analysis process of vast medical diagnostics 3D imaging. The approach can be integrated on a classification network backbone (e.g., Inception, ResNet, etc.). It is noted that the approach does not use local annotation of a segmented tumor for the CNN to train. The approach can rely on label-as-a-global label per slice (i.e., tumor/no tumor) and an annotation of the volume slice in which the tumor seems to be the largest. It is noted that the output of classification process are predictions that are translated into labels.

The approach leverages a main principle/concept that relies on the fact that the tumor area (as seen in the slices) can be described as a continuous and smooth function over the slices sequence. Typically, one can derive this function for a given volume, the maximum value of this function corresponds to the slice with the largest tumor area. However, deriving this function is not an easy task, thus an approximation method is proposed followed by a post processing method in order to reduce approximation noise.

The approach (i.e., selecting the significant slice from a medical diagnostic 3D volume) can be summarized by the following steps: i) infer a "tumor growth" classifier on sliding window of the volume slices. A "tumor growth" classifier predicts for a list of consecutive slices whether the tumor area in that list is growing, declining or not visible, ii) create a discrete integral function out of the classifier predictions over all the slices in the volume, iii) apply post processing on the function of step ii (including a smoothing function and a bias correction) and iv) select the slice index of maximum value of the step iii (i.e., resulted function) as the significant slice.

Other embodiments of the present invention can address the deficiencies in the current art by including algorithms that can segment the tumor in each slice. One of deficiencies includes calculating the segmented area in each slice and selecting the slice with the largest calculated area. The accuracy of such methods depends on a very accurate algorithm at the pixel level that segments the tumor in each slice. In contrast, the approach of the embodiment is based on a slice level accuracy algorithm that classifies whether there is a tumor in a slice. Thus, the approach can presumably be more accurate. Moreover, such segmentation-based algorithms of the current art are difficult to develop since it depend on a local annotation, while embodiment depends on a global annotation.

Other embodiments of the present invention can address the deficiencies in the current art by determining step of inferring a "tumor growth" classifier on sliding window of the volume slices. A "tumor growth" classifier predicts for a list of consecutive slices whether the tumor in that list is growing, declining or not visible. After determining the classifier, embodiment can create a discrete integral function out of the classifier predictions over all the slices in the volume. Embodiment can apply a post-processing step on the discrete integral function, including a smoothing function and a bias correction. Furthermore, embodiment can select the slice index of the maximum value of the resulted function (from the post-processing step) as the significant slice.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether or not explicitly described.

It should be understood that the Figures are merely schematic and are not drawn to scale. It should also be understood that the same reference numerals are used throughout the Figures to indicate the same or similar parts.

FIG. 1 is a functional block diagram illustrating an image detection model environment, designated as 100, in accordance with an embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Image detection model environment 100 includes product network 101, client computing device 102 and server 110.

Network 101 can be, for example, a telecommunications network, a local area network (LAN), a wide area network (WAN), such as the Internet, or a combination of the three, and can include wired, wireless, or fiber optic connections. Network 101 can include one or more wired and/or wireless networks that are capable of receiving and transmitting data, voice, and/or video signals, including multimedia signals that include voice, data, and video information. In general, network 101 can be any combination of connections and protocols that can support communications between server 110, client computing device 102 and other computing devices (not shown) within image detection model environment 100. It is noted that other computing devices can include, but is not limited to, client computing device 102 and any electromechanical devices capable of carrying out a series of computing instructions.

Server 110 and client computing device 102 can be a standalone computing device, a management server, a web server, a mobile computing device, or any other electronic device or computing system capable of receiving, sending, and processing data. In other embodiments, server 110 and client computing device 102 can represent a server computing system utilizing multiple computers as a server system, such as in a cloud computing environment. In another embodiment, server 110 and client computing device 102 can be a laptop computer, a tablet computer, a netbook computer, a personal computer (PC), a desktop computer, a personal digital assistant (PDA), a smart phone, or any other programmable electronic device capable of communicating other computing devices (not shown) within image detection model environment 100 via network 101. In another embodiment, server 110 and client computing device 102 represents a computing system utilizing clustered computers and components (e.g., database server computers, application server computers, etc.) that act as a single pool of seamless resources when accessed within image detection model environment 100.

Client computing device 102 can include a cluster of medical imaging machines and medical diagnostic platforms. Client computing device 102 can also store medical images and 3D scans of various areas of the body that may contain cancerous tumor/growths.

Embodiment of the present invention can reside on server 110. Server 110 includes detection component 111 and database 116.

Detection component 111 provides the capability of detecting/identifying cancerous lesions in multi-view (i.e., 3 dimensional) medical images with an improved performance over existing techniques, and especially to improve detection specificity.

Database 116 is a repository for data used by detection component 111. Database 116 can be implemented with any type of storage device capable of storing data and configuration files that can be accessed and utilized by server 110, such as a database server, a hard disk drive, or a flash memory. Database 116 uses one or more of a plurality of techniques known in the art to store a plurality of information. In the depicted embodiment, database 116 resides on server 110. In another embodiment, database 116 may reside elsewhere within image detection model environment 100, provided that detection component 111 has access to database 116. Database 116 may store information associated with, but is not limited to, radiology reports and results, notes relating to the prognosis by the doctor, multiple medical image data, regression equations and functions, regression models associated with medical image detection, benchmark datasets and testing datasets associated with medical image models.

Figure 2A:
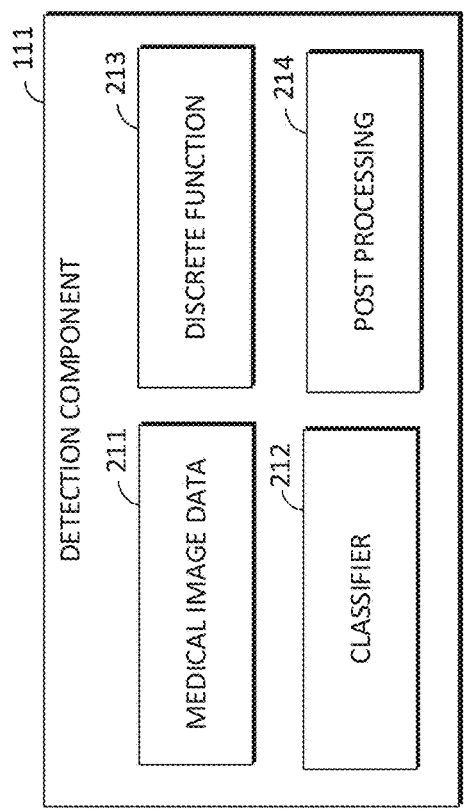
FIG. 2A is a functional block diagram illustrating detection component 111, designated as 200A, in accordance with an embodiment of the present invention.

FIG. 2 is a functional block diagram illustrating detection component 111 in accordance with an embodiment of the present invention. Essentially, the functionality of detection component 111 includes, i) inferring a "tumor growth" classifier on sliding window of the volume slices, ii) creating a discrete integral function out of the classifier predictions over all the slices in the volume, iii) applying post processing on the function of step ii, including a smoothing function and a bias correction and iv) select the slice index of maximum value of the step iii result function as the significant slice. In the depicted embodiment, detection component 111 includes medical image data component 211, classifier component 212, discrete function component 213 and post processing component 214.

A use case will be used to illustrate the components. For example, assume that there are seven slices in an MRI volume, cs=3, k=1, the tumor appears in slices 4-6 and the significant slice is 4. It is noted that the example used is related to tumor slices from the upper front torso of a patient. However, the approach can be used for detection of any cancerous tumor/lesions for any part of the human body.

As is further described herein below, medical image data component 211 of the present invention provides the capability of communicating (i.e., sending and receiving data) with client computing device 102. Data can include medical imaging data associated with patients. Referring to the use case example, medical image data component 211 would retrieve the 3D volume from a medical imaging system.

As is further described herein below, classifier component 212 of the present invention provides the capability of classifying medical images with distinct labels based on a "tumor growth" classification algorithm (e.g., CNN based classifier). The classification is performed on sliding window of the volume slices. The idea of "sliding window" is applying an algorithm sequentially to each slice of the 3D volume with respect to nearest slices. The number of slices that are considered are the "window size". In the "tumor growth" classification algorithm, the classifier uses information from a certain slice and some slices before and after in order to capture the tumor growing trend. Classifier component 212 classifies a predefined number of consecutive slices, cs, to one of three classes: (1) there is no visible tumor, (2) the area of the tumor is growing (pre-tumor), (3) the area of tumor is declining (post-tumor). For each of this classes, embodiment can define a constant step size and that is the class label. For the first class, embodiment set the label to "0". The label is set to "k" and "−k" for the second and third classes respectively (where k is some positive integer). Referring to the previous use case example, classifier component 212 predicts the following labels over a sliding window of the volume slices: slices 1-3: 0; slices 2-4: 1; slices 3-4: 1; slices 4-6: 1; slices 4-7: −1. It is noted that the output of classifier component 212 are predictions that are translated into labels (i.e., −k, k, 0). Additionally, a training typically involved with the classification model, the embodiment can leverage a standard optimizer.

Figure 2B:
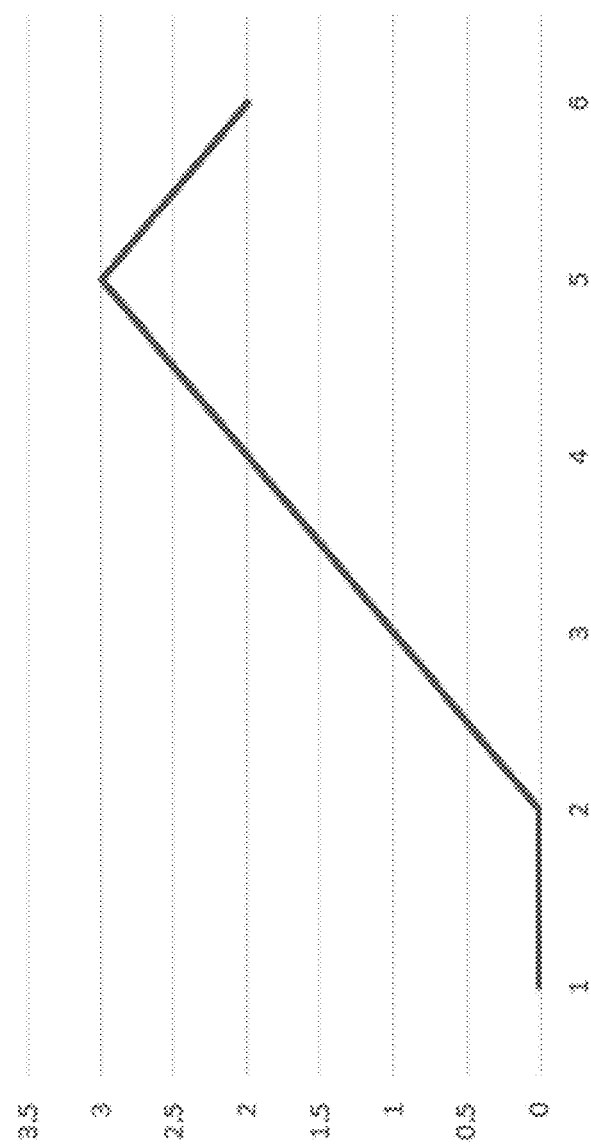
FIG. 2B is an example of a discrete integral function, designated as 200B, in accordance with an embodiment of the present invention.

As is further described herein below, discrete function component 213 of the present invention provides the capability of applying an approximation function on the data from classifier component 212. The approximation function can be defined as using a discrete integral function which is applied over the labels of lists (i.e., list of consecutive volume slices). The lists of consecutive slices are selected via a sliding window over all the volume slices. A discrete integral function are functions that can be defined from a field of mathematical study (e.g., discrete calculus, etc.) that involves the study of incremental change. An example of a discrete integral function for is depicted in attached Figure (FIG. 2B). Referring to the previous use case example, discrete function component 213 applies the discrete integral function (from FIG. 2B) to volume of slices.

As is further described herein below, post processing component 214 of the present invention provides the capability of i) applying a smoothing function, ii) performing a bias correction on result from discrete function component 213 and iii) finding the significant slice. The approximation method (i.e., applying discrete integral function) may include noise, which is mainly due to the statistical error of the classification algorithm and the underlying assumption that the step size is constant. Therefore, a filtering method is applied to the discrete integral function to get a smoother function (e.g., remove noise, etc.), followed by a bias correction to have pre-tumor and post-tumor common integral value. A filtering method may be any smoothing function for removing noise in a signal, for example: averaging window.

Moreover, in cases where there are some prior knowledge about the tumor shape (i.e., that can be reflected in the area function), the knowledge can be used by a Least Square Error (LSE) method to get more accurate approximation function. For example, if there is prior knowledge that the tumor is very concentrated and spherical, embodiment can perform an LSE method for a parabola in order to reduce approximation noise. However, when embodiment does not have any prior knowledge about the tumor shape, it can skip steps i and ii and just apply argmax to get the index of the most significant slice. However, for the presented application of tumors, the assumption (i.e., tumor shape of spherical and concentrated) is valid.

The bias correction is applied to get the integral value of pre and post tumor to be equal. The value of the integral function post tumor is set to the value of the pre tumor integral value.

Lastly, post processing component 214 can find the significant slice by finding index of the slices in which the integral intensity is at a maximum. Post processing component 214 can use a mathematical method of "arguments of the maxima" (known as "arg max" or "argmax"). Argmax are the points or elements of a domain of some function at which the function values are maximized. Argmax refers to inputs at which the function output are as large as possible, in contrast to global maxima. Referring to the previous use case example, post processing component 214 can apply a bias correction which will force the value of the "right tail" of the integral function, currently with [x,y] value of [6,2] and set it to the y value of the "left tail" of the integral function to be [6,0]. And post processing component 214 can use argmax to find significant slice, 4.

Figure 3:
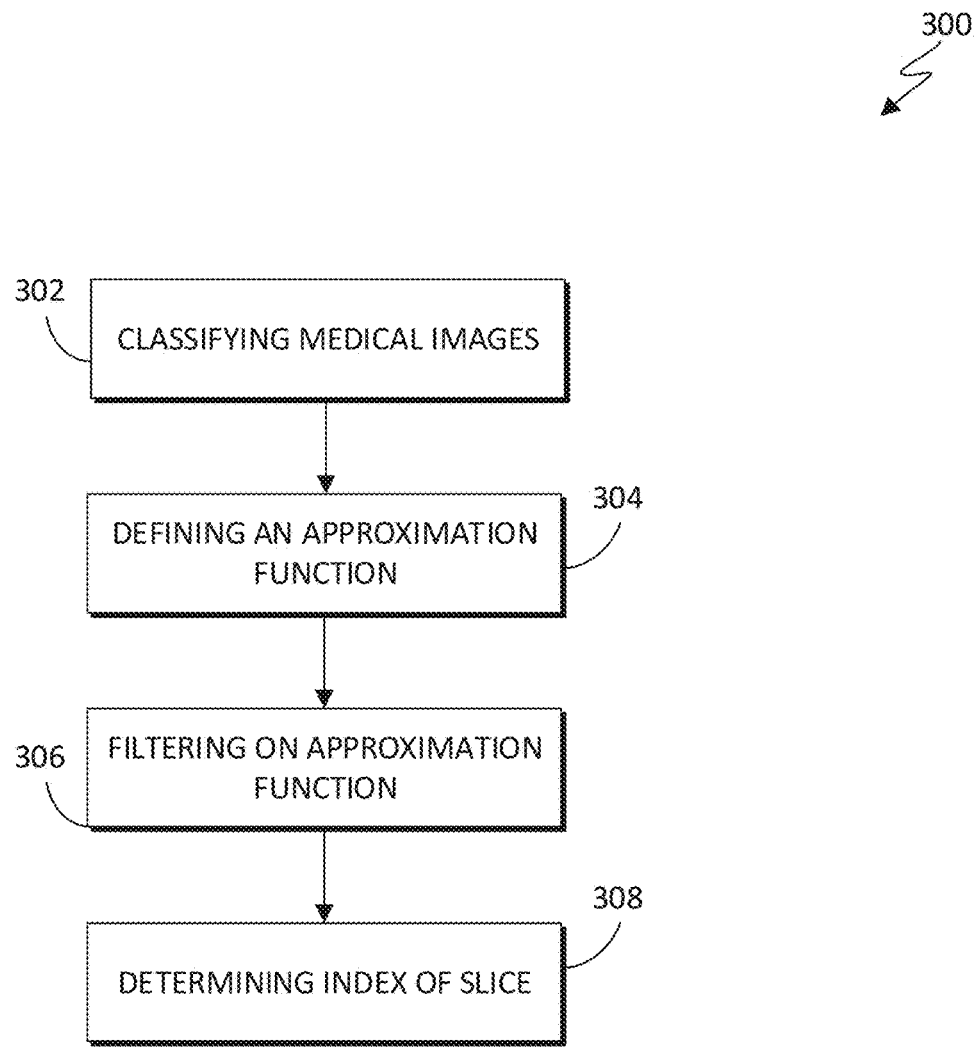
FIG. 3 is a high-level flowchart illustrating the operation of detection component 111, designated as 300, in accordance with an embodiment of the present invention.

FIG. 3 is a flowchart illustrating the operation of detection component 111, designated as 300, in accordance with another embodiment of the present invention.

Detection component 111 classifies medical images (step 302). In an embodiment, detection component 111, through medical image data component 211, retrieves medical image data from client computing device 102. Detection component 111, through classifier component 212 classifies/labels the volume slices. Referring to the prior use case, assume that there are seven slices in an MRI volume, cs=3, k=1, the tumor appears in slices 4-6 and the significant slice is 4. Classifier component 212 predicts the following labels over a sliding window of the volume slices: slices 1-3: 0; slices 2-4: 1; slices 3-4: 1; slices 4-6: 1; slices 4-7: 1.

Detection component 111 defines approximation function (step 304). In an embodiment, detection component 111, through discrete function component 213, defines and applies a discrete integral function (see FIG. 2B) to the use case scenario.

Detection component 111 filters on approximation function (step 306). In an embodiment, detection component 111, through post processing component 214, applies a smoothing function and performs a bias correction. For example, referring to the previous use case, post processing component 214 can use either LSE or averaging window for smoothing. And post processing component 214 can apply a bias correction which will force the value of the "right tail" of the integral function, currently with [x,y] value of [6,2] and set it to the y value of the "left tail" of the integral function to be [6,0].

Detection component 111 determines index of slice (step 308). In an embodiment, detection component 111, through post processing component 214, finds the argmax of data from the previous step. For example, referring to the previous use case, the argmax is used and significant slice, 4 is selected.

Figure 4:
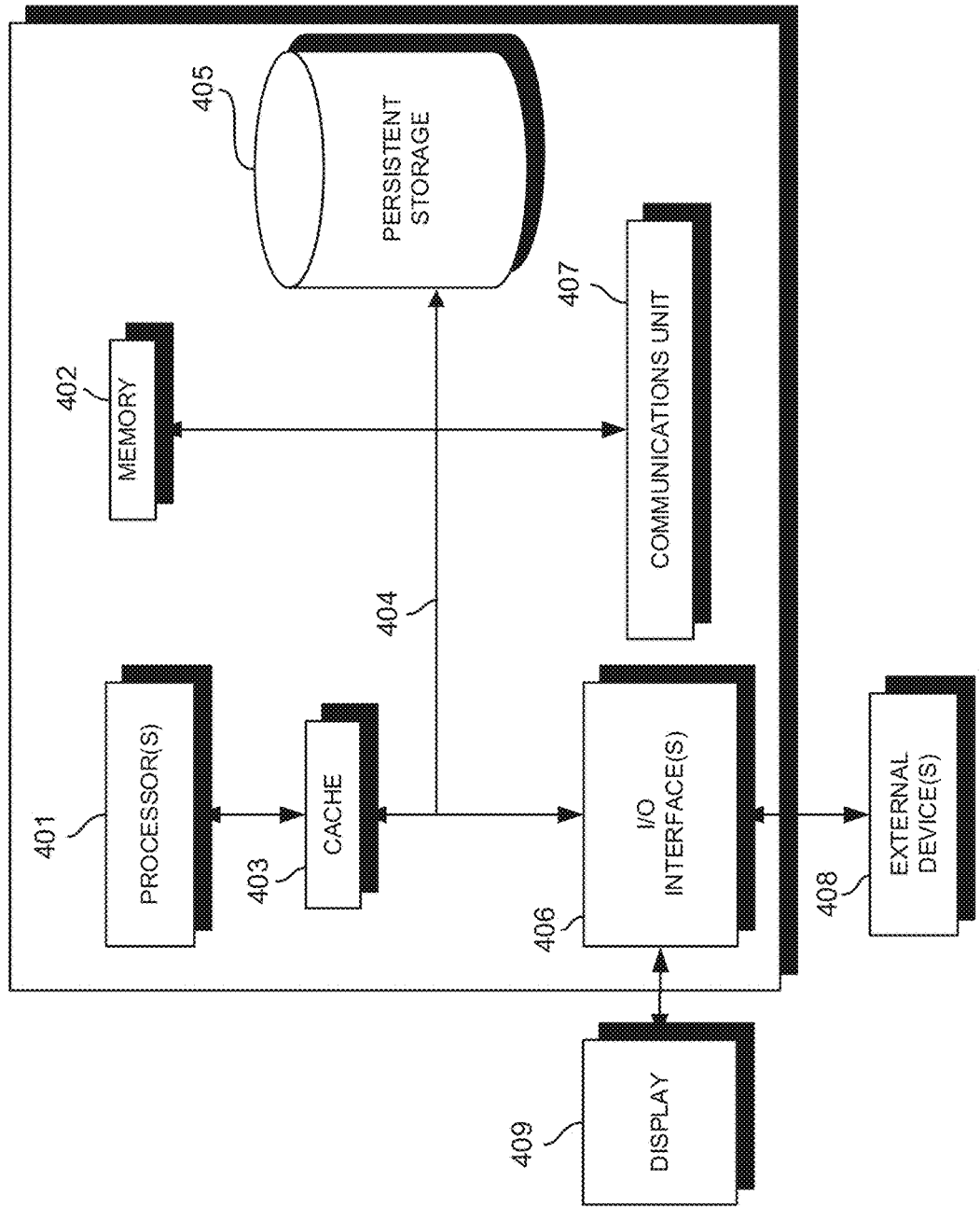
FIG. 4 depicts a block diagram, designated as 400, of components of a server computer capable of executing the detection component 111 within the image detection model environment, of FIG. 1, in accordance with an embodiment of the present invention.

FIG. 4, designated as 400, depicts a block diagram of components of detection component 111 application, in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

FIG. 4 includes processor(s) 401, cache 403, memory 402, persistent storage 405, communications unit 407, input/output (I/O) interface(s) 406, and communications fabric 404. Communications fabric 404 provides communications between cache 403, memory 402, persistent storage 405, communications unit 407, and input/output (I/O) interface(s) 406. Communications fabric 404 can be implemented with any architecture designed for passing data and/or control information between processors (such as microprocessors, communications and network processors, etc.), system memory, peripheral devices, and any other hardware components within a system. For example, communications fabric 404 can be implemented with one or more buses or a crossbar switch.

Memory 402 and persistent storage 405 are computer readable storage media. In this embodiment, memory 402 includes random access memory (RAM). In general, memory 402 can include any suitable volatile or non-volatile computer readable storage media. Cache 403 is a fast memory that enhances the performance of processor(s) 401 by holding recently accessed data, and data near recently accessed data, from memory 402.

Program instructions and data (e.g., software and data x10) used to practice embodiments of the present invention may be stored in persistent storage 405 and in memory 402 for execution by one or more of the respective processor(s) 401 via cache 403. In an embodiment, persistent storage 405 includes a magnetic hard disk drive. Alternatively, or in addition to a magnetic hard disk drive, persistent storage 405 can include a solid state hard drive, a semiconductor storage device, a read-only memory (ROM), an erasable programmable read-only memory (EPROM), a flash memory, or any other computer readable storage media that is capable of storing program instructions or digital information.

The media used by persistent storage 405 may also be removable. For example, a removable hard drive may be used for persistent storage 405. Other examples include optical and magnetic disks, thumb drives, and smart cards that are inserted into a drive for transfer onto another computer readable storage medium that is also part of persistent storage 405. Detection component 111 can be stored in persistent storage 405 for access and/or execution by one or more of the respective processor(s) 401 via cache 403.

Communications unit 407, in these examples, provides for communications with other data processing systems or devices. In these examples, communications unit 407 includes one or more network interface cards. Communications unit 407 may provide communications through the use of either or both physical and wireless communications links. Program instructions and data (e.g., Detection component 111) used to practice embodiments of the present invention may be downloaded to persistent storage 405 through communications unit 407.

I/O interface(s) 406 allows for input and output of data with other devices that may be connected to each computer system. For example, I/O interface(s) 406 may provide a connection to external device(s) 408, such as a keyboard, a keypad, a touch screen, and/or some other suitable input device. External device(s) 408 can also include portable computer readable storage media, such as, for example, thumb drives, portable optical or magnetic disks, and memory cards. Program instructions and data (e.g., Detection component 111) used to practice embodiments of the present invention can be stored on such portable computer readable storage media and can be loaded onto persistent storage 405 via I/O interface(s) 406. I/O interface(s) 406 also connect to display 409.

Display 409 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method for determining a significant slice associated with a tumor from a volume of medical images, the computer-method comprising:
    classifying medical images from a 3D (3 dimensional) medical image database;
    defining approximation function on the classified medical images;
    filtering on the approximation function; and
    determining a significant slice from the filtered approximation function.

2. The computer-implemented method of claim 1, wherein classifying the medical images from the 3D medical image database further comprises:
    labeling, leveraging a CNN (Convoluted Neural Network) based classifier, one or more consecutive slices from the database into three classes, wherein the first of the three classes is labeled as "No Visible Tumor", a second of the three classes is labeled as "Pre-Tumor" and a third of the three classes is labeled as "Post-Tumor".

3. The computer-implemented method of claim 2, wherein defining the approximation function on the classified medical images further comprises:
    creating the approximate function based the one or more consecutive slices, wherein the approximation is a discrete integral function.

4. The computer-implemented method of claim 3, wherein filtering on the approximation function further comprises:
    applying a smoothing function on the approximation function; and
    performing a bias correction on the smoothing function.

5. The computer-implemented method of claim 4, wherein determining a significant slice from the filtered approximation function further comprises:
    determining an arguments of a maxima of the smoothing function.

6. The computer-implemented method of claim 1, wherein the 3D medical image database further comprises MRI (Magnetic Resonance Imaging) scans, CT (Computerized tomography) scans and Tomosynthesis scans.

7. The computer-implemented method of claim 4, wherein the smoothing function further comprises a least square error function.

8. A computer program product for determining a significant slice associated with a tumor from a volume of medical images, the computer program product comprising:
one or more computer readable storage media and program instructions stored on the one or more computer readable storage media, the program instructions comprising:
program instructions to classify medical images from a 3D (3 dimensional) medical image database;
program instructions to define approximation function on the classified medical images;
program instructions to filter on the approximation function; and
program instructions to determine a significant slice from the filtered approximation function.

9. The computer program product of claim 8, wherein program instructions to classify the medical images from the 3D medical image database further comprises:
program instructions to label, leveraging a CNN (Convoluted Neural Network) based classifier, one or more consecutive slices from the database into three classes, wherein the first of the three classes is labeled as "No Visible Tumor", a second of the three classes is labeled as "Pre-Tumor" and a third of the three classes is labeled as "Post-Tumor".

10. The computer program product of claim 9, wherein program instructions to define the approximation function on the classified medical images further comprises:
program instructions to create the approximate function based the one or more consecutive slices, wherein the approximation is a discrete integral function.

11. The computer program product of claim 10, wherein program instructions to filter on the approximation function further comprises:
program instructions to apply a smoothing function on the approximation function; and
program instructions to perform a bias correction on the smoothing function.

12. The computer program product of claim 11, wherein program instructions to determine a significant slice from the filtered approximation function further comprises:
program instructions to determine an arguments of a maxima of the smoothing function.

13. The computer program product of claim 11, wherein the smoothing function further comprises a least square error function.

14. A computer system for determining a significant slice associated with a tumor from a volume of medical images, the computer system comprising:
one or more computer processors;
one or more computer readable storage media;
program instructions stored on the one or more computer readable storage media for execution by at least one of the one or more computer processors, the program instructions comprising:
program instructions to classify medical images from a 3D (3 dimensional) medical image database;
program instructions to define approximation function on the classified medical images;
program instructions to filter on the approximation function; and
program instructions to determine a significant slice from the filtered approximation function.

15. The computer system of claim 14, wherein program instructions to classify the medical images from the 3D medical image database further comprises:
program instructions to label, leveraging a CNN (Convoluted Neural Network) based classifier, one or more consecutive slices from the database into three classes, wherein the first of the three classes is labeled as "No Visible Tumor", a second of the three classes is labeled as "Pre-Tumor" and a third of the three classes is labeled as "Post-Tumor".

16. The computer system of claim 15, wherein program instructions to define the approximation function on the classified medical images further comprises:
program instructions to create the approximate function based the one or more consecutive slices, wherein the approximation is a discrete integral function.

17. The computer system of claim 16, wherein program instructions to filter on the approximation function further comprises:
program instructions to apply a smoothing function on the approximation function; and
program instructions to perform a bias correction on the smoothing function.

18. The computer system of claim 17, wherein program instructions to determine a significant slice from the filtered approximation function further comprises:
program instructions to determine an arguments of a maxima of the smoothing function.

19. The computer system of claim 17, wherein the smoothing function further comprises a least square error function.

20. The computer system of claim 14, wherein the 3D medical image database further comprises MRI (Magnetic Resonance Imaging) scans, CT (Computerized tomography) scans and Tomosynthesis scans.

* * * * *